United States Patent

Ruch

[11] Patent Number: 6,092,236
[45] Date of Patent: Jul. 25, 2000

[54] PASSIVE GLOVE FOR PLASTIC DEFORMATION OF HAND EXTENSORS AND FLEXORS

[76] Inventor: William J. Ruch, 536-45th St., Oakland, Calif. 94609

[21] Appl. No.: 09/119,699

[22] Filed: Jul. 21, 1998

[51] Int. Cl.[7] ............................................. A41D 19/00
[52] U.S. Cl. ........................................... 2/159; 2/158
[58] Field of Search ........................... 2/16, 158, 159, 2/160, 161.4, 161.7, 162, 163, 161.1; 482/44, 45, 46, 47, 105; 601/40; 602/36, 64, 75

[56] References Cited

U.S. PATENT DOCUMENTS

| | | | |
|---|---|---|---|
| 1,457,858 | 6/1923 | Ruddell | 2/158 |
| 2,736,034 | 2/1956 | Fredenhagen et al. . | |
| 3,838,853 | 10/1974 | Fredenhagen . | |
| 4,104,740 | 8/1978 | Rinehart | 2/158 |
| 4,247,097 | 1/1981 | Schwartz | 2/159 |
| 4,253,660 | 3/1981 | Tiktin . | |
| 4,556,215 | 12/1985 | Tarbox et al. | 2/159 |
| 4,684,123 | 8/1987 | Fabry | 2/159 |
| 4,830,360 | 5/1989 | Carr, Jr. . | |
| 4,911,433 | 3/1990 | Walker et al. . | |
| 4,923,418 | 5/1990 | Hoffman | 441/57 |
| 5,300,000 | 4/1994 | Schwartz . | |
| 5,409,447 | 4/1995 | Wedge, Jr. . | |
| 5,453,064 | 9/1995 | Williams, Jr. . | |
| 5,476,439 | 12/1995 | Robinson . | |
| 5,492,525 | 2/1996 | Gibney . | |
| 5,527,244 | 6/1996 | Waller et al. . | |
| 5,538,488 | 7/1996 | Villepigue . | |
| 5,667,466 | 9/1997 | Riley, Jr. . | |

OTHER PUBLICATIONS

A copy of a Meyer Distributing Co. advertisement for Chattanooga Group, Inc. "Carpal Trac", p. 1.
Zatoon, Zae, "Carpal Tunnel Relief?," http://www.angelfire.com/ct/Zatoon/carpaltunnel.html, ©1998 Zae Zatoon, Ph.D., pp. 1–5.
"Carpal Tunnel Procedure," Web document at http://www.spinecenter.com/endoscopic.html, pp. 1–5.
Montgomery, Kate, "New Article: CTS Research By Kate Montgomery," http://www.sportstouch.com/cts.htm, pp. 1–7.

Primary Examiner—John J. Calvert
Assistant Examiner—Gary L. Welch
Attorney, Agent, or Firm—Townsend and Townsend and Crew LLP

[57] ABSTRACT

A passive, or anti-exercise, glove designed to produce plastic deformation of the flexors and/or the extensors of an arm by permanently lengthening the muscle tissue or the implicated tendon or tendons. The lengthened muscle/tendon relieves the stress on the carpal tunnel and permits the spacing surrounding the wrist bones to return to a non-compacted condition. Pressure on the median nerve is relieved and the repetitive strain injury is mitigated. The glove includes an enclosure defining a hand receiving region complementary to a hand of a user, the enclosure further defining a weight receiving region adapted to receive a user selectable weight such that the weight receiving region encapsulates the hand receiving region; and a mechanism, coupled to the enclosure, for securing the enclosure to the user.

9 Claims, 3 Drawing Sheets

PASSIVE GLOVE FOR PLASTIC DEFORMATION OF HAND EXTENSORS AND FLEXORS

BACKGROUND OF THE INVENTION

The invention relates generally to a device and method for relief of symptoms of repetitive strain injuries and more specifically to plastic deformation of connective tissues in the hand and forearm.

There are many contemporaneous references describing a common type of repetitive strain injury (RSI) referred to as carpal tunnel syndrome. This syndrome results from an abnormal condition of the 'carpus,' the human wrist. The carpus consists of eight bones arranged into two rows. The bones closest to the hand form a channel referred to as the carpal tunnel. This channel provides the conduit for the median nerve and the tendons and arteries connected to the thumb and fingers.

The detailed anatomy of the tendons passing through the carpus is well-documented and beyond the scope of this application. FIG. 1 and FIG. 2 illustrate, in a simplistic way, the main muscle/tendon structures implicated in the preferred embodiment. FIG. 1 is a view of the superficial muscle layer of the front of the left forearm. There are five muscles: the pronator radii teres, the flexor carpi radialis, the flexor carpi ulnaris, the flexor sublimis digitorum, and the palmaris longus. FIG. 2 is a view of the deep muscle layer of the front of the left forearm. There are three muscles: the flexor profundus digitorum, the flexor longus pollicis, and the pronator quadratus.

These muscles of the superficial layer extend from the internal condyle (near the elbow) past the carpus to the hand. For the deep layer, the muscles begin at the upper three-fourths of the anterior and inner surfaces of the ulna and extend past the carpus to the tips of the fingers. These muscles include tendon structures that connect to the bones of the hands. Many of these tendons pass through the carpal tunnel, and some pass under an annular ligament that surrounds a portion of the carpus.

When the carpal tunnel becomes restricted, such as inflammation of soft tissues of the wrist and the carpal tunnel, pressure is applied to the median nerve. Such pressure results in pain, tingling and numbness in the hand and fingers. The soft tissues may become inflamed from injury, arthritis, repetitive motion or from no particularly obvious cause.

X-ray examination of the carpus of persons suffering from certain types of carpal tunnel syndrome have shown compaction of the spaces surrounding the wrist bones, particularly the longitudinal spacing. One conventional treatment to relieve carpal tunnel syndrome is to cut the annular ligament. Once cut, spacing surrounding the wrist bones temporarily increases, particularly laterally. However, once separated laterally, the wrist bones may be more susceptible to further longitudinal compacting, possibly further aggravating the condition.

Other treatments for carpal tunnel syndrome include exercises designed to improve the strength of the forearm muscles. Unfortunately, the exercises recreate the environment that is implicated in creating the laterally compacted wrist bone condition. Exercises, like repetitive actions, are a form of resistance training that results in the strengthening of the forearm muscles responsible for clenching the fingers and thumb. Muscles, in response to resistance training, become stronger by increasing the number and density of muscle fibers. Unfortunately, the strength increase is typically asymmetric, with the clenching muscles becoming stronger than the corresponding 'unclenching' muscles due to the nature of the repetitive stress. (In other cases, the flexors and extensors (the clenching and unclenching muscles) may both become strengthened and result in compaction of the effected joint.) The asymmetric strengthening of the clenching muscles causes increased stress on the carpal tunnel and longitudinally compacts the wrist bones.

The prior art includes various types and configurations of exercise gloves specifically designed to enhance and build one or more muscles of the hand and/or forearm. Such devices are active devices and use of these devices in the preferred way is believed to exacerbate the conditions addressed by the present invention.

SUMMARY OF THE INVENTION

The present invention addresses an apparatus and method to relieve the anatomical imbalances caused by repetitive strain injuries, particularly of the hand/wrist/forearm. As opposed to the exercise gloves of the prior art, the preferred embodiment is a passive glove designed to counter effects induced or contributed to by exercise. The preferred embodiment of the invention includes this passive, or anti-exercise, glove designed to produce plastic deformation of the flexors and/or the extensors by permanently lengthening the muscle tissue or the implicated tendon or tendons. The lengthened muscle/tendon relieves the stress on the carpal tunnel and permits the spacing surrounding the wrist bones to return to a non-compacted condition. Pressure on the median nerve is relieved and the repetitive strain injury is mitigated.

In the preferred embodiment, the invention includes an apparatus that includes an enclosure defining a hand receiving region complementary to a hand of a user, the enclosure further defining a weight receiving region adapted to receive a user selectable weight such that the weight receiving region encapsulates the hand receiving region; and a mechanism, coupled to the enclosure, for securing the enclosure to the user.

In operation, the user attaches a passive glove to the hand attached to the limb undergoing treatment. The passive glove, in the preferred embodiment, includes a hand enclosure that is surrounded by a weight-containing region and that, most preferably, isolates the individual fingers and the thumb so that the user selectable weight fully extends the flexors and/or the extensors from the tips of the individual fingers back to the connection near the elbow. The user preferably permits the gloved hand to depend (hang) for the treatment period sufficiently long to induce plastic deformation of the appropriate flexors/extensors undergoing treatment.

Reference to the remaining portions of the specification, including the drawing and claims, will realize other features and advantages of the present invention. Further features and advantages of the present invention, as well as the structure and operation of various embodiments of the present invention, are described in detail below with respect to accompanying drawing. In the drawing, like reference numbers indicate identical or functionally similar elements.

DESCRIPTION OF THE SPECIFIC EMBODIMENTS

Figure 1:
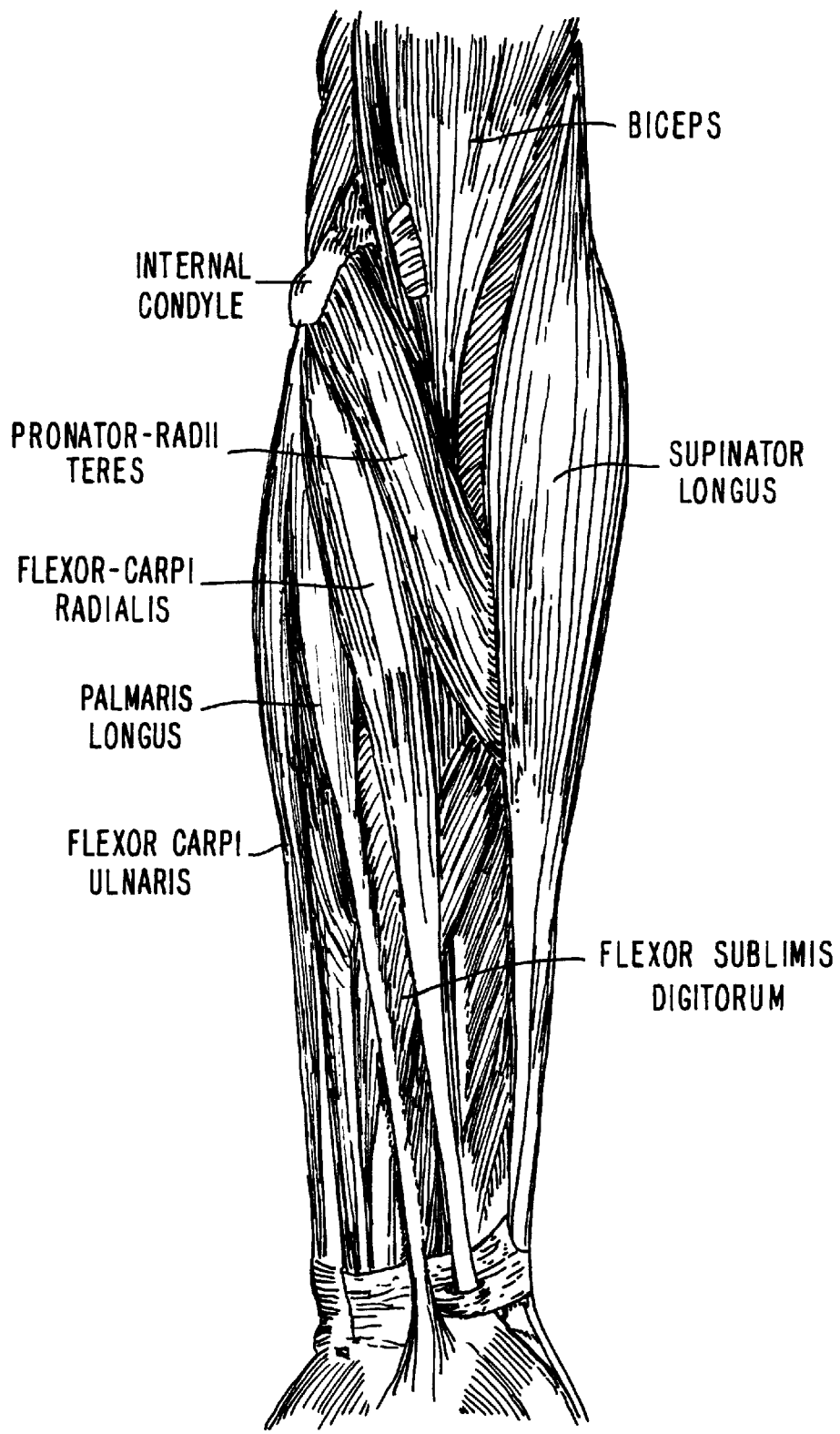
FIG. 1 is a view of the superficial muscle layer of the front of the left forearm.
Figure 2:
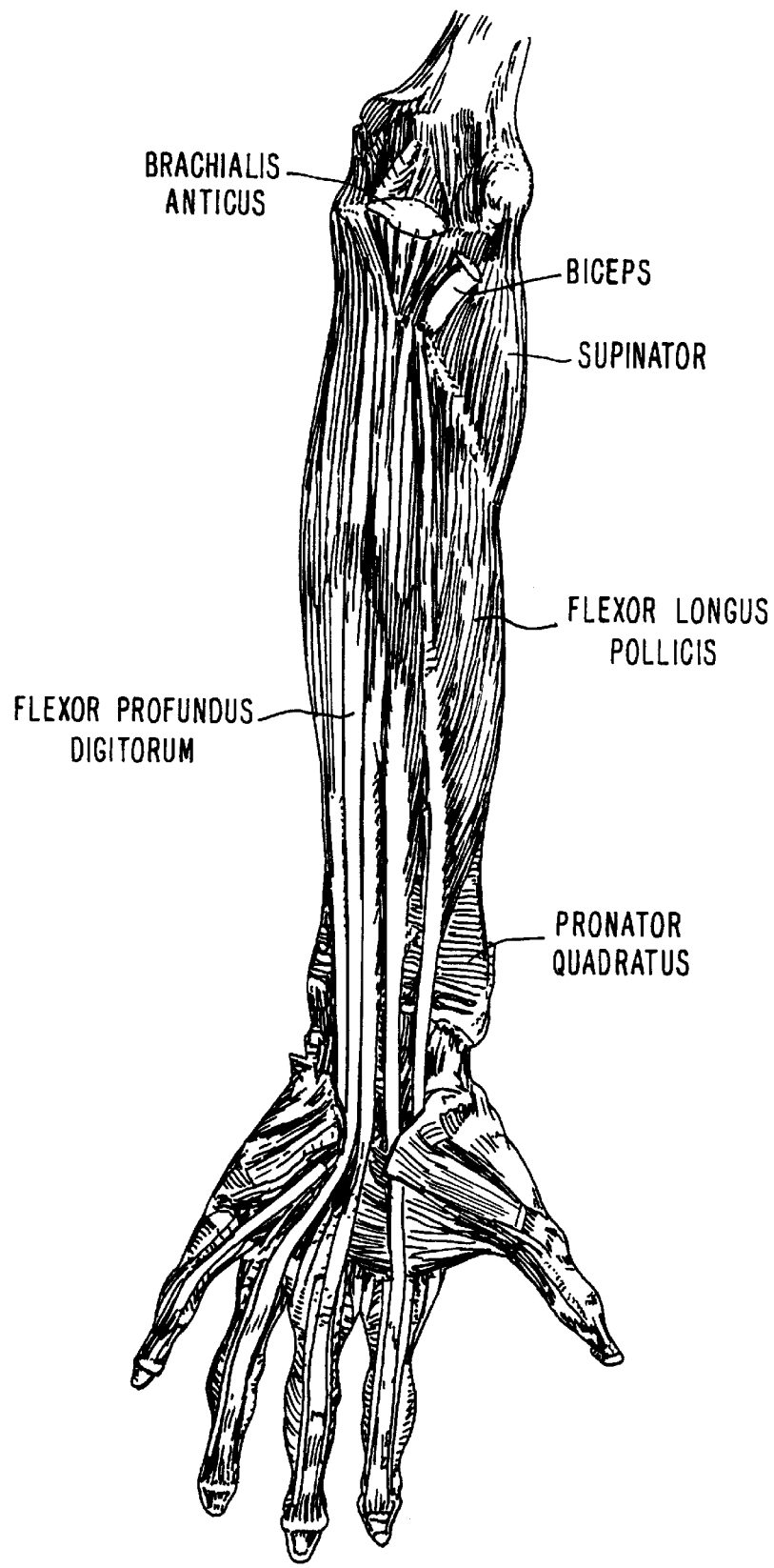
FIG. 2 is a view of the deep muscle layer of the front of the left forearm.
Figure 3:
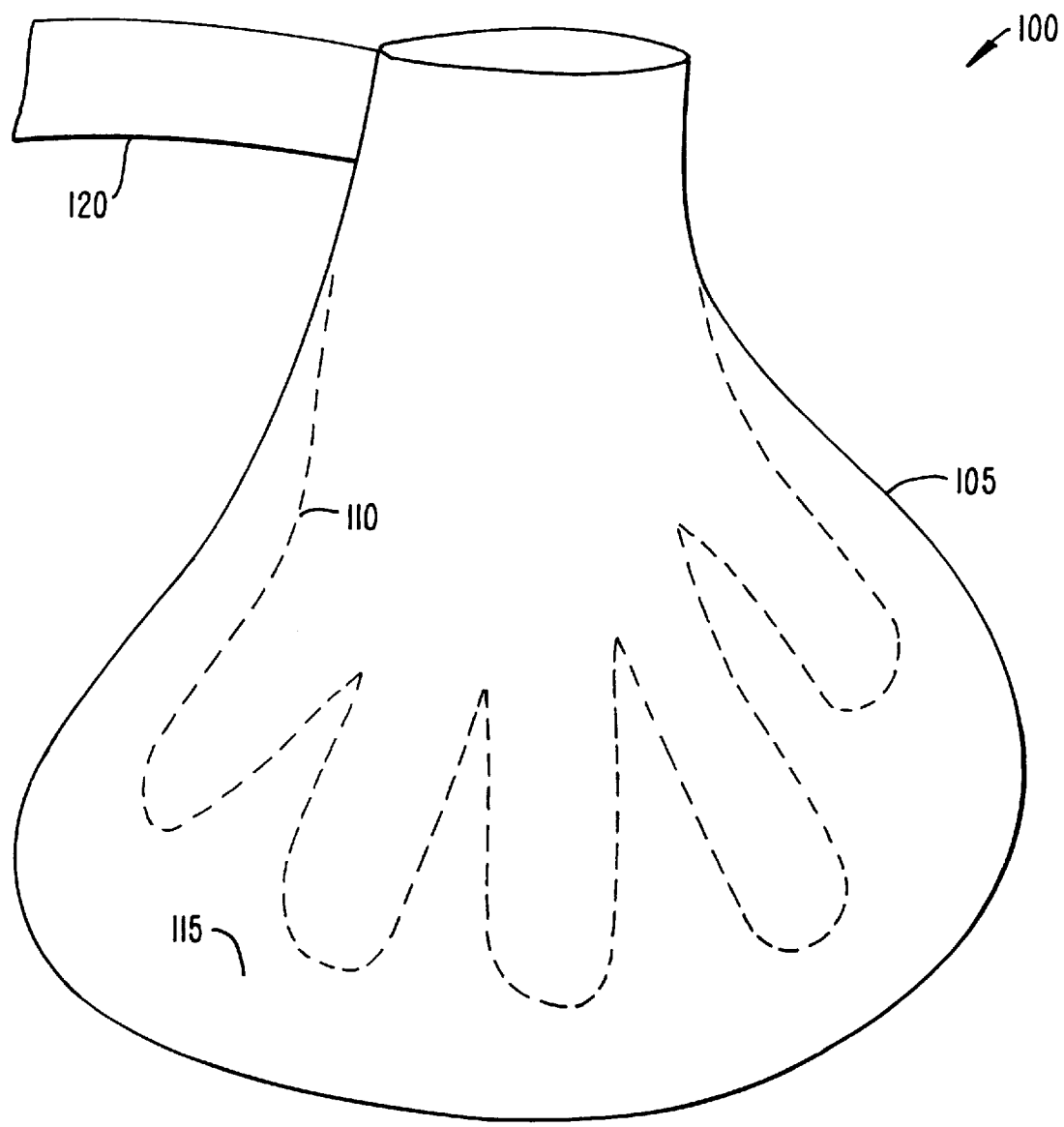
FIG. 3 is a front elevation view of a passive glove.

FIG. 3 is a front elevation view of a passive glove 100. Glove 100 includes an enclosure 105 defining a hand-receiving region 110 and a weight-receiving region 115. In addition, an attachment system 120 equipped with, for example, a strap having a hook and loop mating system permits passive glove 100 to be secured to the hand of a user.

Enclosure 105 is a two-layer construction of flexible fabric wherein hand-receiving region 110 is formed in enclosure 105 to produce complementary weight-receiving region 115. Hand-receiving region 110, in the preferred embodiment, is shaped similarly to a glove to separate and isolate the individual fingers. Other shapes or digit arrangements may be used depending upon the desired treatment profile. Other materials and designs for the construction are possible.

Weight-receiving region 115 surrounds and supports hand-receiving region 110. It is a desired goal to apply the plastic lengthening inducing force to the entire appropriate surface of the extremity undergoing treatment. For example, for the carpal tunnel syndrome, it is desirable to evenly apply the appropriate force to the surfaces of all the fingers and to the thumb.

In operation, the user selects an appropriately sized passive glove 105 sized according to the hand size of the user. An appropriate amount of weight is added to passive glove 105 and the user secures passive glove 105 to the hand using attachment system 120. The user then permits the hand to freely hang, aligning the upper and lower arms, the wrist and the hand. The alignment with the dependent weight loads and stretches the flexors and extensors through application of the force directly over the length of the fingers. The user maintains the passive state of the hand, wrist, and arm for the entire treatment period. The periodic and prolonged use of passive glove 100 causes plastic deformation of the flexors and extensors in the forearm, resulting in reduction of the symptoms of carpal tunnel syndrome.

In the preferred embodiment, there are three sizes of glove: large, medium and small. The large size includes about two pounds of steel shot, the medium size includes about one and one-half pounds of shot, and the small size includes about one pound of shot. The treatment time is designed to achieve a lengthening of the tendon structure. Some studies have shown that a minimum loading time of about fifteen minutes is necessary before any lengthening may occur. Hence, twenty minutes is believed to be the minimum treatment time for any glove. The large size has treatment time of twenty to sixty minutes, the medium size has a treatment time of twenty to forty minutes, and the small size is twenty to thirty minutes. The recommended schedule is once to three times daily for these durations.

In conclusion, the present invention provides a simple, efficient, passive non-surgical solution to a problem of treating certain types of repetitive strain injuries. While the above is a complete description of the preferred embodiments of the invention, various alternatives, modifications, and equivalents may be used. It would be possible to fashion a similar implement for treating other types of joints, appendages and conditions. Therefore, the above description should not be taken as limiting the scope of the invention which is defined by the appended claims.

What is claimed is:

1. A stretching system for stretching at least one of muscles, tendons and ligaments, the system comprising:

at least two gloves, each glove defining a hand receiving region for receiving a hand of a user and a weight retaining region encompassing a distal periphery of the hand receiving region; and means within the encompassed weight retaining region for providing gravitational stress for streching muscles;

wherein the at least two gloves are different sizes with respect to one another in order to fit different hand sizes.

2. A system in accordance with claim 1 wherein the system comprises three gloves.

3. A system in accordance with claim 2 wherein the three gloves include a small sized glove, a medium sized glove and a large sized glove.

4. A system in accordance with claim 3 wherein the small sized glove includes approximately one pound of material within the weight retaining region, the medium sized glove includes approximately one and a half pounds of material within the weight retaining region, and the large sized glove includes approximately two pounds of material within the weight retaining region.

5. A system in accordance with claim 1 wherein the hand receiving region of each glove isolates fingers of the hand from each other when the hand is received within the hand receiving region.

6. A system in accordance with claim 1 wherein the material within the weight retaining region of each glove substantially evenly distributes the weight of the material at a terminus of extensors and flexors of the hand received within the hand receiving region.

7. A glove for stretching at least one of muscles, tendons and ligaments, the glove comprising:

a hand receiving region for receiving a hand of a user;

a weight retaining region encompassing a distal periphery of the hand receiving region; and means within the encompassed weight retaining region for providing gravitational stress for stretching muscles.

8. A glove in accordance with claim 7 wherein the hand receiving region isolates fingers of the hand from each other when the hand is received within the hand receiving region.

9. A glove in accordance with claim 7 wherein the material within the weight retaining region substantially evenly distributes the weight of the material at a terminus of extensors and flexors of the hand received within the hand receiving region.

* * * * *